United States Patent
Figueira et al.

[11] Patent Number: 6,122,539
[45] Date of Patent: Sep. 19, 2000

[54] METHOD FOR VERIFYING ACCURACY DURING INTRA-OPERATIVE MR IMAGING

[75] Inventors: Michael R. Figueira, Waukesha, Wis.; Erik Penner, Wesel, Germany; Robert G. Keen, New Berlin, Wis.

[73] Assignee: General Electric Company, Milwaukee, Wis.

[21] Appl. No.: 09/499,787

[22] Filed: Feb. 8, 2000

Related U.S. Application Data

[63] Continuation of application No. 09/001,883, Dec. 31, 1997.

[51] Int. Cl.⁷ .................................................. A61B 5/055
[52] U.S. Cl. ........................ 600/411; 600/414; 324/307; 324/309
[58] Field of Search ................................. 600/407, 410, 600/411, 414, 417, 426, 427, 429; 606/130; 324/307, 309

[56] References Cited

U.S. PATENT DOCUMENTS

| | | |
|---|---|---|
| 5,230,338 | 7/1993 | Allen et al. . |
| 5,368,030 | 11/1994 | Zinreich et al. . |
| 5,383,454 | 1/1995 | Bucholz . |
| 5,469,847 | 11/1995 | Zinreich et al. . |
| 5,551,429 | 9/1996 | Fitzpatrick et al. . |
| 5,617,857 | 4/1997 | Chander et al. . |
| 5,622,170 | 4/1997 | Schulz . |
| 5,682,890 | 11/1997 | Kormos et al. ......................... 600/417 |
| 5,769,861 | 6/1998 | Vilsmeier ............................... 606/130 |
| 5,820,553 | 10/1998 | Hughes ................................. 600/426 |
| 5,848,967 | 12/1998 | Cosman ................................ 600/426 |

*Primary Examiner*—Ruth S. Smith
*Attorney, Agent, or Firm*—Quarles & Brady; Christian G. Cabou; Phyllis Y. Price

[57] ABSTRACT

An MRI system operates in a realtime mode to produce images rapidly for a physician performing a medical procedure. The location of the medical instrument used in the procedure is monitored by a locator system which produces an icon on the images to show where the instrument is positioned. Reference phantoms are used by the physician to confirm that the system is properly calibrated to accurately display the instrument location.

14 Claims, 4 Drawing Sheets

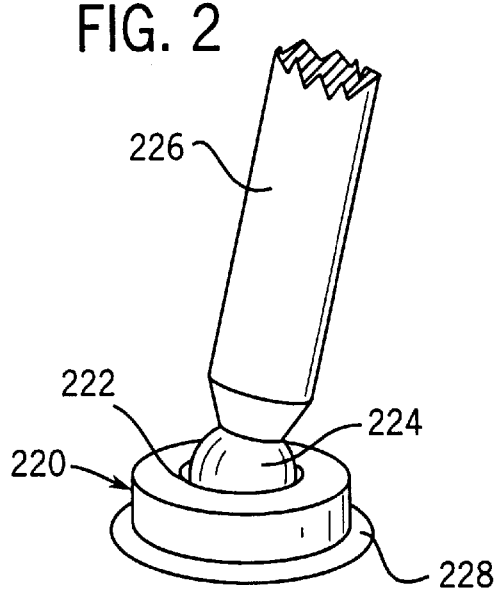
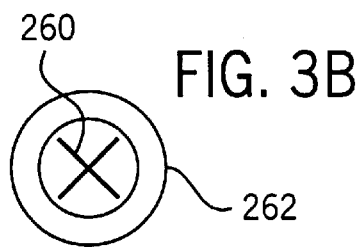
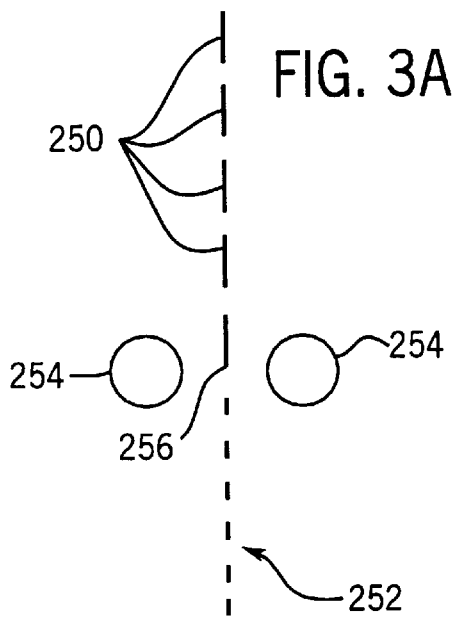
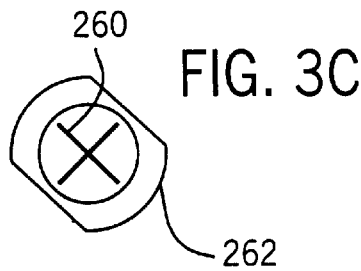

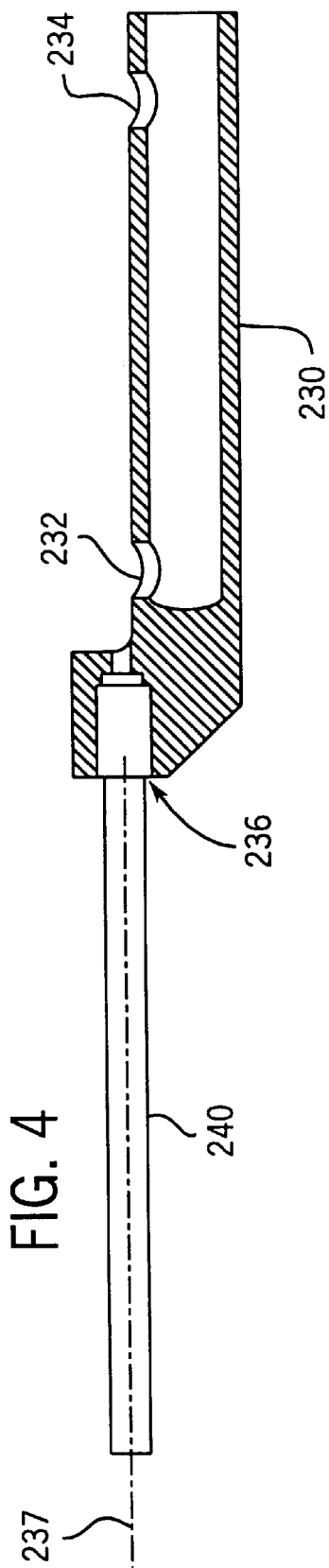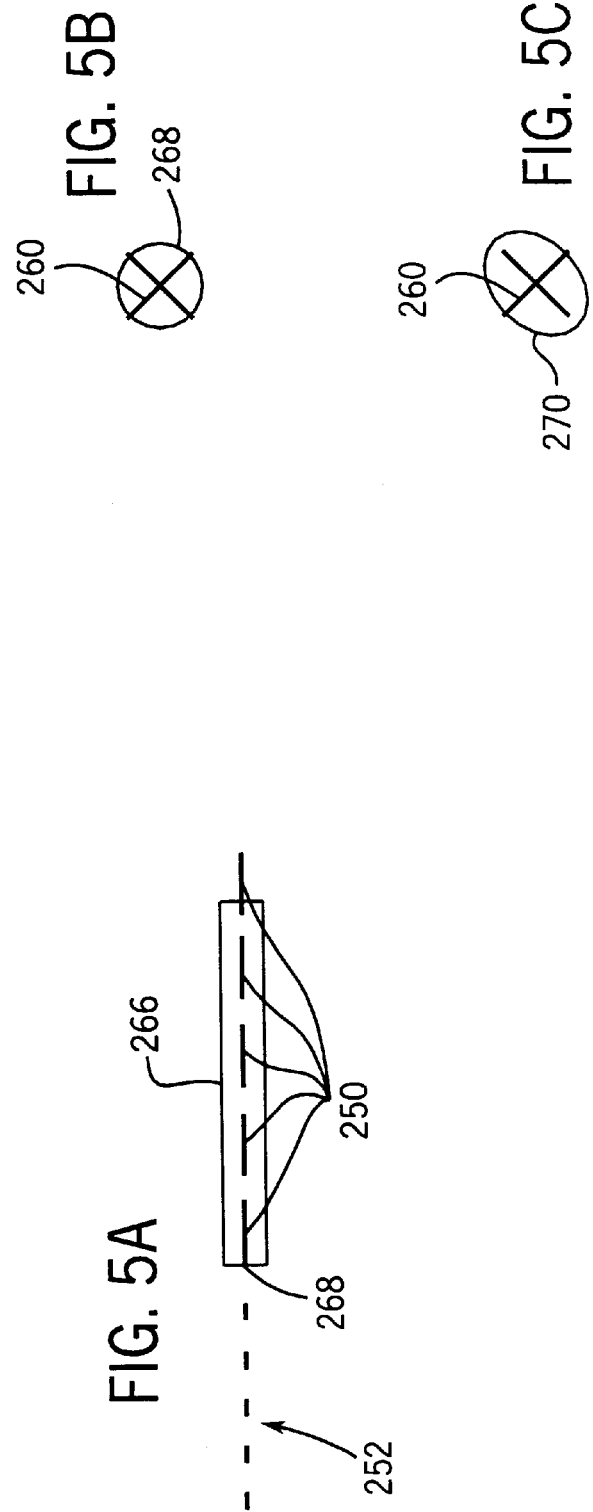

METHOD FOR VERIFYING ACCURACY DURING INTRA-OPERATIVE MR IMAGING

This application is a continuation of Ser. No. 09/001,883 filed Dec. 31, 1997.

BACKGROUND OF THE INVENTION

The field of the invention is nuclear magnetic resonance imaging methods and systems. More particularly, the invention relates to intra-operative MR imaging in which a medical instrument is guided by acquiring realtime images.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Intra-operative MR imaging is employed during a medical procedure to assist the doctor in guiding an instrument. For example, during a needle biopsy the MRI system is operated in a realtime mode in which image frames are produced at a high rate so that the doctor can monitor the location of the needle as it is inserted. The needles can cause artifacts on the images that allow the clinician to observe their location. However, in some instances the image prescriptions and the needle material may combine to render the artifact so small that the needle cannot be easily detected or so large that the needle cannot be localized.

A locator device such as that sold commercially by Image Guided Technologies, Inc. under the trademark "Flashpoint" and described in U.S. Pat. Nos. 5,622,170 and 5,617,857 may be used to track the location of the instrument and provide coordinate values to the MRI system which enable it to mark the location of the instrument in each reconstructed image. The medical instrument is attached to a handpiece that is manipulated by the physician and whose position is detected by surrounding sensors. For example, the handpiece may emit light from two or more light emitting diodes which is sensed by three stationary cameras.

Because the coordinate system of the locator device is separate from the coordinate system of the MRI system, the location of the instrument as measured by the locator device must be transformed to the MRI system coordinates to accurately indicate the instrument location in the reconstructed image. This transformation is accomplished using a transformation matrix which is created off-line using a calibration procedure. The calibration procedure is an elaborate and time consuming process which is performed periodically by maintenance personnel. If the calibration is inaccurate, the location of the instrument in the image displayed to the doctor is inaccurate. This is unacceptable in procedures that rely on an accurate placement of the instrument in the imaged patient. Furthermore, it is possible to select from a range of handpieces with a range of needle lengths. A simple method of verifying the system accuracy and correct selection of handpieces and needle lengths would increase the clinician confidence in the system and possibly prevent adverse events.

SUMMARY OF THE INVENTION

The present invention is a method for verifying the accuracy of a locator system during an intra-operative MR imaging procedure. More specifically, the invention includes placing a reference phantom in the region of interest being imaged, placing a handpiece which forms part of the locator system in a known physical location relative to the reference phantom, acquiring an image that includes the reference phantom, and annotating the reconstructed image with an icon that indicates the handpiece position. When the system is accurately calibrated, the handpiece is indicated in the expected position relative to the reference phantom and any inaccuracy is easily seen.

A general object of the invention is to enable the physician to check the accuracy of a locating system during an intra-operative MR imaging procedure. In one embodiment the reference phantom is attached to the handpiece which is moved to arbitrary locations in the region of interest. If inaccuracies are present, the images produced by the MRI system reveal changes in the relative positions of the reference phantom and the handpiece icon. In another embodiment the instrument attached to the handpiece is replaced with an extension which is positioned near a separate reference phantom. Inaccuracies are revealed if the handpiece icon in the image is not in the same position with respect to the imaged reference phantom.

BRIEF DESCRIPTION OF THE DRAWINGS

FIG. 2 is a first embodiment of the reference phantom;

FIGS. 3a–c are pictorial representations of the images produced when the reference phantom of FIG. 2 is employed;

FIG. 4 is a second embodiment of the reference phantom which is attached to a handpiece;

FIGS. 5a–c are pictorial representations of the images produced when the reference phantom of FIG. 4 is employed.

DESCRIPTION OF THE PREFERRED EMBODIMENT

Figure 1:
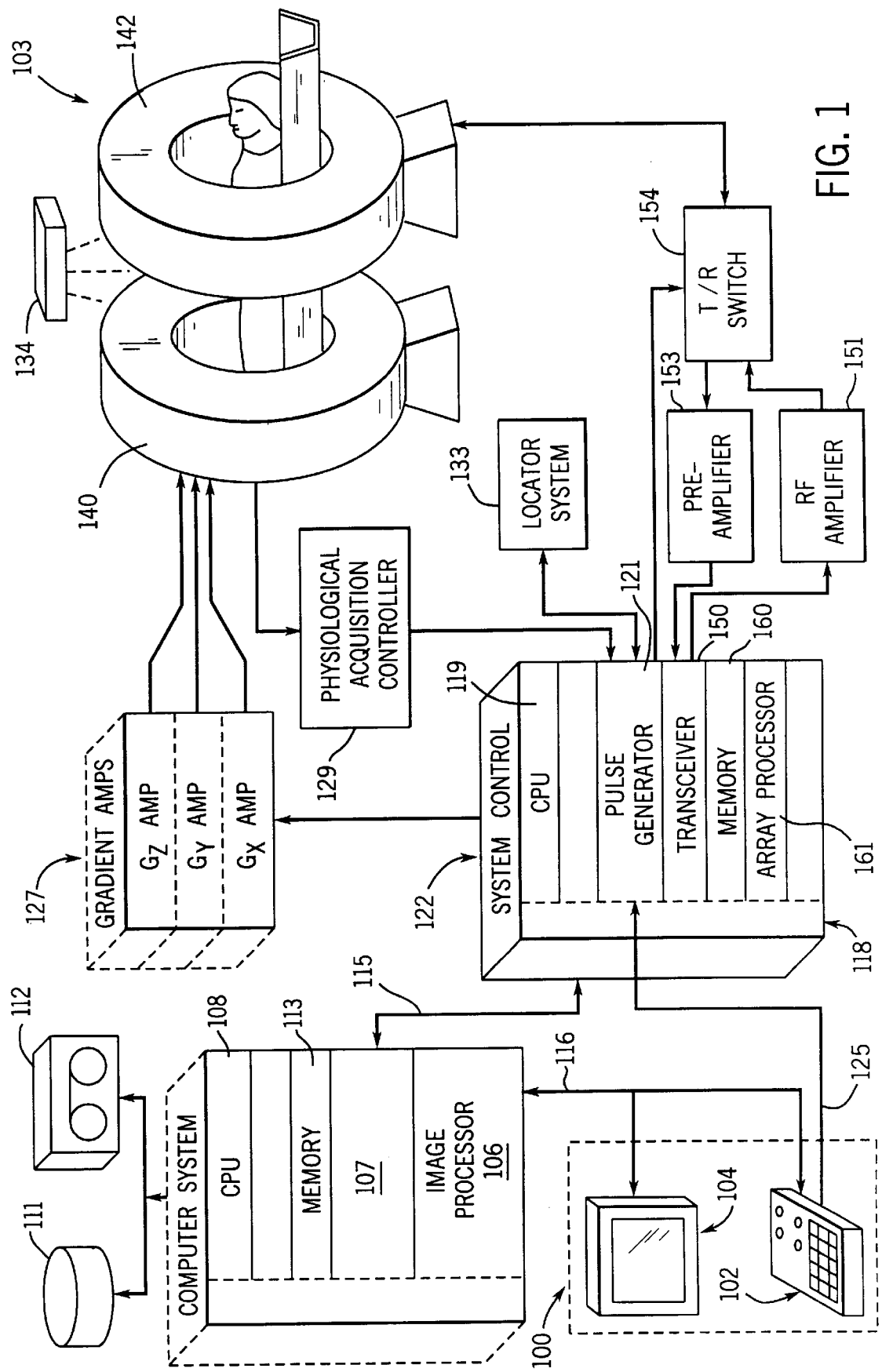
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. A separate display(not shown) is also located near the magnet system 103 so that they are available to a physician attending the subject of an MRI scan. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a locator system 133 which receives signals from a sensor assembly 134 mounted above the magnet system 103. As described in U.S. Pat. Nos. 5,617,857 and 5,622,170, which are incorporated herein by reference, the locator system 133 includes a work station that provides the location of a handpiece 230 that is manipulated by a physician performing a procedure. As is described in more detail below, this location data is employed by the pulse generator module 121 to position the slice acquisition. This location data is also used to produce an icon on the reconstructed image which indicates the location therein of the instrument attached to the handpiece 230.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in the magnet system 103 to produce the magnetic field gradients used for position encoding acquired signals. A transceiver module 150 in the system control 122 produces pulses which are amplified by an RF amplifier 151 and coupled to an RF coil in the magnet assembly 103 by a transmit/receive switch 154. The resulting signals radiated by the excited nuclei in the patient may be sensed by the same RF coil and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the RF coil during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil are digitized by the transceiver module 150 and transferred to a memory module 160 in the system control 122. When an array of k-space data has been acquired in the memory module 160, an array processor 161 operates to Fourier transform the k-space data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Referring particularly to FIG. 1, when an intra-operative MR imaging procedure is conducted a patient is placed in the magnet system 103 and a region of interest in the patient is aligned in the system isocenter located between the two, spaced magnet rings 140 and 142. A physician standing between magnet rings 140 and 142 has unrestricted access to the region of interest in the patient and can manipulate the handpiece 230 to perform a medical procedure such as a needle biopsy. The sensor assembly 134 monitors the position of the LEDs 232 and 234 on the handpiece 230 and communicates their position to the locator system 133. The locator system 133 decodes these positions and produces the handpiece tip position, needle trajectory vector and a transverse normal vector value. The workstation associated with the locator system 133 employs this handpiece position data along with user supplied needle information (e.g. length and offset) and system calibration data to compute the actual needle location.

Figure 6:
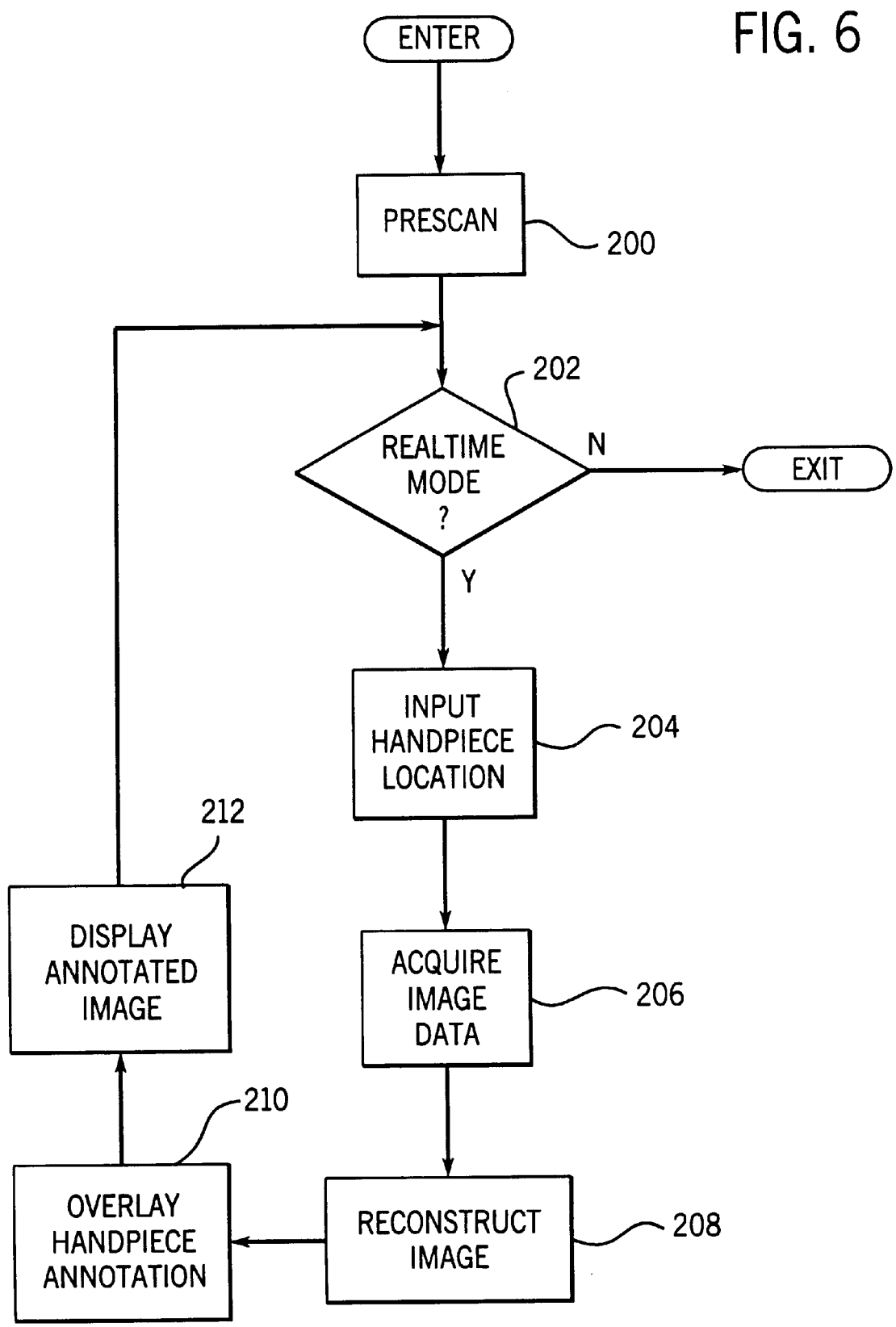
FIG. 6 is a flow chart of the realtime scanning process performed by the MRI system of FIG. 1.

The physician may employ the MRI system to both plan the procedure and to assist in performing the procedure. Referring particularly to FIG. 6, after performing the usual prescan functions indicated at process block 200, the MRI system may be switched to a realtime mode in which it continuously scans the patient and produces frame images that are displayed to the attending physician. Depending on the particular pulse sequence prescribed image frames may be produced every 0.7 to 14.0 seconds to provide the physician with realtime information regarding the location of the medical instrument.

While the MRI system is in the interactive mode, as determined at decision block 202, the handpiece location data is input at process block 204 and used to guide the imaging process. More specifically, the handpiece location data is employed by the pulse generator module 121 to alter the imaging pulse sequence by changing the amplitude of gradient pulses and/or the frequency of RF excitation pulses to acquire the image from the indicated handpiece location. Two-dimensional slice images are acquired and the center of the acquired image is set to the indicated handpiece location (usually the tip of the medical instrument being used). The orientation of the acquired slice image can be selected to remain fixed with respect to the MRI system (e.g. coronal, sagittal, axial), or it may be oriented with respect to the alignment of the handpiece (e.g. in-plane or perpendicular). In other words, the orientation of the slice images produced during the realtime mode can be set by the physician to best monitor the progress of the procedure.

Referring still to FIG. 6, the image data is then acquired as indicated at process block 206, and a two-dimensional slice image is reconstructed at process block 208 as described above. As indicated at process block 210, a handpiece icon, is then used to annotate the reconstructed image which is displayed as indicated at process block 212. This is accomplished using the handpiece location data to position the icon, and in some cases, orient the icon as will be described below. It should be apparent that the accuracy of the annotation of the reconstructed image is of great importance, since it indicates to the physician the location of the instrument attached to the handpiece with respect to the patient's displayed anatomy, particularly in cases where the artifact of the needle is so small as to render the needle practically invisible. It is this displayed information which the physician uses to guide the medical procedure being performed.

The present invention is a method for assuring the physician that the system is calibrated to properly indicate the instrument location on the displayed image. Calibration methods such as that disclosed in U.S. Pat. No. 5,622,170 may be performed before the procedure is started or at periodic service intervals, however, the present invention provides realtime assurance that calibration is correct.

The method employs a reference phantom that is placed in the region of interest and which is shaped to reveal its location in the acquired images. Referring particularly to FIG. 2, a first embodiment of the reference phantom includes an annular shaped body 220 molded from a polycarbonate material and filled with a 4 mM solution of copper sulfate ($CuSO_4$). This produces a strong NMR signal which results in a bright shape in the reconstructed image. Its outer diameter is 15 mm and its height is 4 mm. The hole 222 defined by the body 220 is sized at 4.5 mm to fit a spherical tip 224 on a handpiece extension 226. An adhesive layer (not shown) is formed on the bottom surface of the reference phantom 220 and a peel-away paper disc 228 is disposed over this layer. When used during a procedure, the disc 228 is peeled away and the reference phantom 220 is placed on the patient in the region of interest. The adhesive provides a sticky surface which holds the phantom 220 in place. At any time during the procedure the physician may remove the medical instrument and attach the handpiece extension 226 to the handpiece 230. The spherical tip 224 is placed in the hole 222 of the reference phantom 220 and the display screen is observed. As will be explained in detail below, the displayed image reveals if the system is properly calibrated.

A second embodiment of the reference phantom is attached directly to the handpiece 230. Referring particularly to FIG. 4, the handpiece 230 is a circular cylindrical structure having two openings 232 and 234 therein through which light emitting diodes (not shown) are directed. The light produced by these LEDs is sensed by the sensor assembly 134 (FIG. 1) mounted overhead. Wiring (not shown) extends from one end of the handpiece 230 and a socket 236 is formed in the other end. A medical instrument such as a needle (not shown) may be attached to the handpiece 230 by inserting it into the socket 236 and fastening it in place with set screws. The instrument extends along a handpiece axis indicated at 237. In the alternative, the handpiece extension 226 discussed above may be inserted in the socket 236, or as shown in FIG. 4, a rod-shaped reference phantom 240 may be attached to the handpiece 230. The reference phantom 240 is a polycarbonate tube having an outside diameter of 0.375 inches and an inside diameter of 0.25 inches. It is filled with a 4 mM solution of copper sulfate ($CuSO_4$) and its length is the same as the medical instrument being used. It produces a strong NMR signal which results in a bright region in the reconstructed MR image. At any time during the medical procedure the physician may attach the reference phantom 240 to the handpiece 230 and place it anywhere in the region of interest to check the system calibration. As will be explained in more detail below, by observing the displayed image the physician can test the accuracy of the system at different locations and angles.

Both of the phantoms can be sterilized so that they can be brought into the surgical field.

Referring particularly to FIGS. 3A–C, an icon representing the location of the handpiece is overlayed on each reconstructed image as described above. In the preferred embodiment, when the instrument lies in the plane of the two-dimensional slice image being produced by the MRI system, this icon includes a series of dashed lines 250 that represent the instrument attached to the handpiece 230 and a dotted line 252 which indicates the trajectory of the instrument if it is advanced into the patient. This is illustrated in FIG. 3A where the image of the reference phantom 220 appears as two bright circles 254 because the slice image is perpendicular to the plane of the reference phantom 220. In the example shown, the tip of the instrument icon located at 256, is precisely in the middle of the phantom image 254. This indicates that the system is precisely calibrated and that the physician can rely on the instrument position indicated by the icon 250.

When the slice image being produced by the MRI system is prescribed as perpendicular to the direction of the instrument, the instrument icon is "X" shaped as shown in FIGS. 3B and 3C at 260. The icon 260 indicates the location in the image of the instrument as determined by the locator system 133, and if the system is properly calibrated, this icon 260 is centered in the circular image 262 of the reference phantom 220. In FIG. 3B the slice image is in the plane of the reference phantom 220, and in FIG. 3C the slice image is at an oblique angle which cuts off parts of the reference phantom 220. In either case the accuracy of the system can be confirmed by the centered icon 260.

When the rod-shaped reference phantom 240 is employed the dashed and dotted line icons 250 and 252 are seen in the reconstructed image as shown in FIG. 5A when the instrument is in the plane of the slice image. The rod-shaped reference phantom 240 appears as a bright, elongated rectangle 266, and if the calibration is proper, the instrument represented by dashed line icon 250 is centered along this rectangle 266 as shown. In addition, the end of the icon 250 aligns exactly with the end of the rectangular phantom image 266 at point 268.

When the rod-shaped reference phantom 240 is employed and the slice image plane is rotated out of the plane of the phantom 240, the "X" icon 260 is displayed as shown in FIGS. 5B and 5C. When the slice image is oriented perpendicular to the axis of the handpiece 230, the reference phantom 240 appears in the image as a bright circular spot 268 as shown in FIG. 5B and the icon 260 is centered in this spot 260 if the system is properly calibrated. If the slice image is at an oblique angle with respect to the axis of the handpiece 230, the phantom 240 appears as a bright elliptical spot 270 as shown in FIG. 5C. When the system is properly calibrated, the locator system 133 places the icon 260 in the center of this ellipse 270.

The present invention can be employed in a number of ways by the physician to check the system calibration during an intra-operative MR scan. The medical instrument is removed from the handpiece 230 and either the handpiece extension 226 or the rod-shaped reference phantom 240 is attached in its place. At each location to be checked in the region of interest, images are acquired and annotated with the icon 250 and 252. Then, the orientation of the image slice is changed to a perpendicular plane and the acquired and reconstructed images are annotated with the icon 260. In this manner, the calibration in three dimensions can be confirmed at each location.

What is claimed is:

1. A method for testing the accuracy of a locator system in an MRI system for producing images of a subject located in a region of interest, which images are guided by the position of a handpiece that is monitored by the locator system, the steps comprising:

placing a reference phantom in the region of interest that produces a visible shape in an image produced by the MRI system;

positioning the handpiece in a predetermined location with respect to the reference phantom;

measuring the position of the handpiece with the locator system and conveying the measured position to the MRI system;

acquiring image data with the MRI system from a location determined by the Position measured by the locator system and reconstructing an image which includes the reference phantom visible shape; and annotating the image with an icon that is positioned on the image at the measured handpiece position such that the icon is displayed in the predetermined location with respect to the reference phantom when the locator system is accurate.

2. The method as recited in claim 1 which includes attaching the reference phantom to the handpiece.

3. The method as recited in claim 1 which includes detaching a medical instrument from the handpiece and attaching the reference phantom in its place.

4. The method as recited in claim 3 which includes shaping the reference phantom into a rod.

5. The method as recited in claim 1 which includes forming an opening in the reference phantom and the handpiece is positioned in said predetermined location by inserting a portion thereof in the opening.

6. The method as recited in claim 5 which includes shaping the reference phantom into a ring.

7. The method as recited in claim 5 which includes interchanging a handpiece extension with a medical instrument attached to the handpiece; and inserting the handpiece extension in the opening.

8. An MRI system for producing images of a subject located in a region of interest, a combination comprising:

a handpiece which may be manipulated in the region of interest to direct a medical procedure on the subject;

a locator system for measuring the location of the handpiece within the region of interest and producing handpiece location data;

a reference phantom placed in the region of interest, the reference phantom being constructed of a material which produces a strong NMR signal and being shaped to produce a distinctive shape in an MR image;

means for acquiring NMR image data from a location in the region of interest determined by the handpiece location data;

means for reconstructing an image from the acquired NMR image data; and means for annotating the reconstructed image with an icon representing the handpiece using the handpiece location data, such that when the locator system accurately measures the location of the handpiece, the icon is displayed in a predetermined location with respect to the distinctive phantom shape.

9. The MRI system as recited in claim 8 in which the reference phantom is attached to the handpiece.

10. The MRI system as recited in claim 8 in which a medical instrument is attached to the handpiece when used in a medical procedure and the reference phantom is attached to the handpiece when used in a calibration check procedure.

11. The MRI system as recited in claim 10 in which the reference phantom is rod-shaped.

12. The MRI system as recited in claim 8 in which the reference phantom has an opening in it and a portion of the handpiece is disposed in the opening when placed in said predetermined location.

13. The MRI system as recited in claim 12 in which the reference phantom is ring-shaped.

14. The MRI system as recited in claim 12 in which the portion of the handpiece disposed in the opening is a handpiece extension which is attached to the handpiece.

* * * * *